(12) United States Patent
Bhumiratana et al.

(10) Patent No.: US 11,179,498 B2
(45) Date of Patent: Nov. 23, 2021

(54) ENGINEERING MECHANICALLY FUNCTIONAL HUMAN CARTILAGE AND METHOD OF MAKING SAME

(71) Applicant: THE TRUSTEES OF COLUMBIA UNIVERSITY IN THE CITY OF NEW YORK, New York, NY (US)

(72) Inventors: Sarindr Bhumiratana, Davis, CA (US); Gordana Vunjak-Novakovic, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 589 days.

(21) Appl. No.: 15/656,681

(22) Filed: Jul. 21, 2017

(65) Prior Publication Data

US 2017/0333597 A1    Nov. 23, 2017

Related U.S. Application Data

(63) Continuation of application No. PCT/US2016/014094, filed on Jan. 20, 2016.

(60) Provisional application No. 62/208,147, filed on Aug. 21, 2015, provisional application No. 62/107,256, filed on Jan. 23, 2015.

(51) Int. Cl.
| | |
|---|---|
| *A61L 27/36* | (2006.01) |
| *A61L 27/38* | (2006.01) |
| *A61L 27/56* | (2006.01) |
| *A61F 2/30* | (2006.01) |
| *A61L 27/46* | (2006.01) |
| *A61L 27/50* | (2006.01) |
| *A61L 27/42* | (2006.01) |

(52) U.S. Cl.
CPC ...... *A61L 27/3612* (2013.01); *A61F 2/30756* (2013.01); *A61L 27/3608* (2013.01); *A61L 27/3834* (2013.01); *A61L 27/425* (2013.01); *A61L 27/46* (2013.01); *A61L 27/50* (2013.01); *A61L 27/56* (2013.01); *A61F 2/3094* (2013.01); *A61F 2002/30762* (2013.01); *A61F 2002/30766* (2013.01); *A61L 2400/06* (2013.01); *A61L 2430/06* (2013.01); *A61L 2430/10* (2013.01)

(58) Field of Classification Search
CPC .. A61L 27/46; A61L 2400/06; A61L 2430/06; A61L 2430/10; A61L 27/3608; A61L 27/3612; A61L 27/3834; A61L 27/425; A61L 27/50; A61L 27/56; C08L 89/06; A61F 2002/30762; A61F 2002/30766; A61F 2/30756; A61F 2/3094
See application file for complete search history.

(56) References Cited

U.S. PATENT DOCUMENTS

| | | |
|---|---|---|
| 6,306,169 B1 | 10/2001 | Lee et al. |
| 2003/0050709 A1 | 3/2003 | Noth et al. |
| 2007/0071733 A1 | 3/2007 | Kandel et al. |
| 2011/0053262 A1 | 3/2011 | Athanasiou et al. |
| 2012/0107783 A1 | 5/2012 | Julian et al. |
| 2014/0314824 A1 | 10/2014 | Kim et al. |

FOREIGN PATENT DOCUMENTS

| | | |
|---|---|---|
| CN | 1746295 | 3/2006 |
| CN | 102085390 | 6/2011 |
| EP | 1537839 | 6/2005 |
| WO | 2006138552 | 12/2006 |
| WO | 2007025290 | 3/2007 |
| WO | 2009154466 | 12/2009 |
| WO | 2010005917 | 1/2010 |

OTHER PUBLICATIONS

Bhumiratana, S. et al. Large, stratified, and mechanically functional human cartilage grown in vitro by mesenchymal condensation. Proceedings of the National Academy of Sciences. May 13, 2014, vol. 111, No. 19.
Hu, JC et al. A self-assembling process in articular cartilage tissue engineering. Tissue Eng. vol. 12 / Issue 4 pp. 969-979, Apr. 2006.
McBride, SH et al. Modulation of stem cell shape and fate B: mechanical modulation of cell shape and gene expression. Tissue Eng Part A, vol. 14 / Issue 9, pp. 1573-1580, Sep. 2008.
CNIPO, First office action mailed for application No. 2016800068660, dated Dec. 30, 2019, 7 Pages.
WIPO, International Preliminary Report on Patentability mailed for application No. PCT/US2016/014094, dated Jul. 25, 2017, 7 pages.
WIPO, International Search Report and Written Opinion mailed for application No. PCT/US2016/014094, dated Mar. 31, 2016, 8 pages.

*Primary Examiner* — Blaine Lankford
(74) *Attorney, Agent, or Firm* — Ballast IP Law, LLP

(57) ABSTRACT

Medical devices having engineered mechanically functional cartilage from adult human mesenchymal stem cells and method for making same.

12 Claims, 30 Drawing Sheets

ENGINEERING MECHANICALLY FUNCTIONAL HUMAN CARTILAGE AND METHOD OF MAKING SAME

CROSS-REFERENCE TO RELATED APPLICATIONS

This application is a continuation of International Application No. PCT/US16/14094, filed Jan. 20, 2016, which claims the benefit of U.S. Provisional Application No. 62/107,256, filed Jan. 23, 2015 and U.S. Provisional Application No. 62/208,147, filed Aug. 21, 2015, the contents of each are hereby incorporated by reference in their entirety.

STATEMENT REGARDING FEDERALLY SPONSORED RESEARCH

This invention was made with government support under grant numbers DE016525 and EB002520, awarded by the National Institutes of Health. The government has certain rights in the invention.

FIELD

The present disclosure relates to the field of tissue engineering, and more particularly to tissue engineering mechanically functional human cartilage.

BACKGROUND

As the world population ages, knee and hip replacements are estimated to increase multifold over the years. In addition, musculoskeletal injuries (e.g., sports injuries) are on the rise, more than doubling in the last decade for the pediatric population.

The generation of functional tissues in vitro from a patient's cells would revolutionize regenerative medicine, by providing biological substitutes for the tissues lost or damaged due to injury, disease, or aging. The growing understanding of embryonic development and stem cell biology has greatly influenced the tissue engineering approaches to scaffold design, cell manipulation, and incorporation of factors (biochemical and physical) that regulate stem cell differentiation and tissue formation.

Tissue engineering is of particular interest to cartilage regeneration, as cartilage exhibits only minimal capability for intrinsic healing due to its avascular nature. The hallmark characteristics of cartilage disease include the loss of mechanical properties, collagen degradation, reduced proteoglycan synthesis, and decreased cellularity. Approaches to the repair of focal cartilage lesions include laser solder welding, autograft cell/tissue transfer via periosteal grafts, mosaicplasty, and the autologous chondrocyte implantation method for cartilage regeneration. While these options offer a temporary relief of symptoms, they also introduce long-term problems.

In cartilage tissue engineering, scaffolding materials have been used with primary bovine chondrocytes to engineer cartilage with properties approximating those of native tissue. However, these methods result in subnormal cartilaginous tissues when used with human mesenchymal stem cells (hMSCs), which are a preferable cell source for clinical application.

Engineering biological substitutes for tissues, or even organs, is becoming increasingly plausible but still faces major hurdles. Cartilage has been the major focus for tissue engineers because it is an avascular tissue containing only one cell type, and was initially considered to be an easy target. For example, cartilage repair by autologous chondrocytes harvested from a patient's knee and expanded in culture provides a cell-therapy product. However, harvesting autologous chondrocytes from the patient's knee is associated with morbidity and risk of arthritis. A different source of cells, such as bone-marrow or adipose hMSCs, would be of high clinical interest, as it would avoid tissue harvest from the knee.

Additionally, autologous and allogeneic hMSCs have been used as a source of trophic factors to induce cartilage regeneration in clinical trials. None of these methods can generate mechanically functional human cartilage. To date, the compositions and mechanical properties of cartilage generated from hMSCs remain inferior to those achieved by chondrocytes. Accordingly, there remains a need for effective tissue engineering of mechanically functional cartilaginous tissue.

SUMMARY

In a first aspect, a medical device comprising engineered human cartilage that is mechanically functional is provided. The engineered cartilage exhibits properties of native human cartilage. For example, but not limitation, the engineered cartilage has a Young's modules of >800 kPa and an equilibrium friction coefficient of <0.3. In other embodiments, the engineered human cartilage has physiological stratification properties, stiffness or tribological properties.

In one embodiment, the engineered human cartilage is attached to a bone substrate. In this regard, the medical device is an implant. In some embodiments, the engineered human cartilage is anatomically shaped and may be used to replace or repair bone. In this respect, medical device and/or engineered cartilage can be clinically sized, e.g., centimeter sized. The bone substrate may be an articular surface of a condyle. The condyle may be configured to correspond to an anatomical human condyle of a patient, for example by imaging the patient's condyle and employing 3D printing techniques for example. Thus, the medical device may be a personalized osteochondral tissue construct for a particular patient. In another embodiment, the engineered cartilage may be used in a delivery device, such as an injection pen, for local delivery to a bone defect.

In another aspect, the subject matter is directed to an anatomical scaffold. The scaffold includes decellularized bone matrix; and condensed mesenchymal bodies. In one embodiment, the condensed mesenchymal bodies form a dense cellular layer disposed on the bone substrate. The dense cellular layer of condensed mesenchymal bodies and the bone substrate form a stratified structure.

In some embodiments, the decellularized bone matrix is porous, and the condensed mesenchymal bodies are interdispersed in the porous matrix. In other words, the condensed mesenchymal bodies penetrate the porous bone to form a construct.

In another aspect, a method for generating an osteochondral construct is provided. The method includes culturing human mesenchymal stem cells to form condensed mesenchymal bodies, then fusing or attaching the condensed mesenchymal bodies on a bone substrate.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

DETAILED DESCRIPTION OF EXEMPLARY EMBODIMENTS

Figure 1:
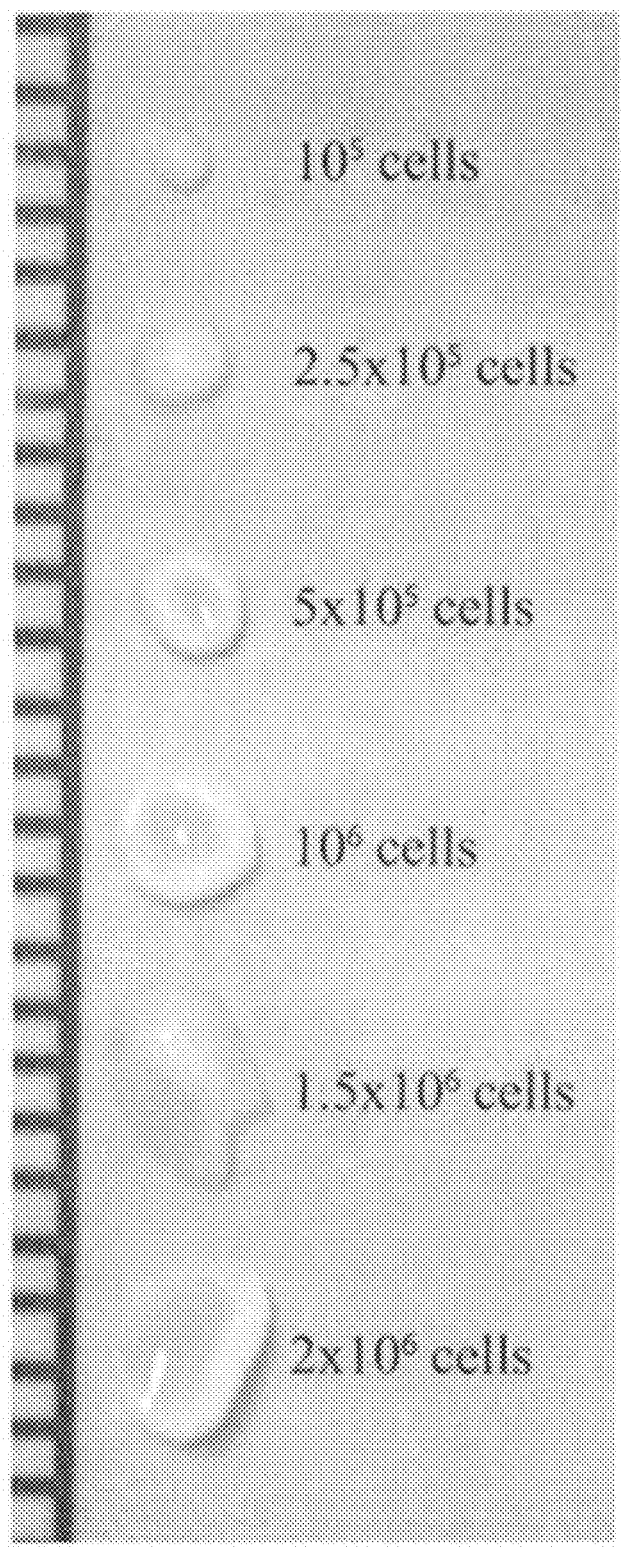
FIG. 1 depicts one embodiment of the disclosed subject matter where day-3 shows CMBs created from $1 \times 10^5$ to $2 \times 10^6$ hMSCs (scale bar: 1 mm). In this embodiment, cell numbers in the range $(1-5) \times 10^5$ resulted in the formation of condensed spherical CMBs, whereas the higher cell numbers resulted in flattened CMBs.

Reference will now be made in detail to exemplary embodiments of the disclosed subject matter. Methods and corresponding steps of the disclosed subject matter will be described in conjunction with the detailed description of the system.

In accordance with one aspect of the present disclosure, engineered human cartilage with physiologic stratification and biomechanics is provided. In accordance with one exemplary embodiment, a medical device comprising the engineered human cartilage is provided. The medical device can be configured to be a plug or an implant. The plug comprising engineered human cartilage can plug a defect in a subject. The plug is capable of integrating with the subject's tissue. In another embodiment, the medical device is an implant. The implant comprise the engineered human cartilage secured to a bone substrate.

In another aspect, a method for engineering mechanically functional human cartilage is described. With respect to the method, it has been surprisingly found that when exposed to transforming growth factor-ß, mesenchymal stem cells are induced to condense into cellular bodies, undergo chondrogenic differentiation, and form cartilaginous tissue that exhibits properties similar to native human cartilage. Prior art methods for making engineered human cartilage have failed in forming mechanically functional human cartilage that exhibits properties similar to native human cartilage.

In one exemplary embodiment, the condensed mesenchymal cell bodies (CMBs) formed in vitro set an outer boundary after about 5 days of culture, as indicated by the expression of mesenchymal condensation genes and deposition of tenascin. Before setting of boundaries, the CMBs are fused into homogenous cellular aggregates giving rise to well-differentiated and mechanically functional cartilage. The mesenchymal condensation and fusion of CMBs is used to grow centimeter-sized, anatomically shaped pieces of human articular cartilage over 5 week of culture. The biomechanical properties of the cartilage formed from this method are comparable to native human cartilage. In one embodiment, the engineered cartilage has a Young's modulus of >800 kPa and an equilibrium friction coefficient of <0.3. Prior methods of engineering cartilage have not attained these properties. It has been found that the CMBs have the capability of forming a mechanically strong cartilage-cartilage interface in an in vitro cartilage defect model. The CMBs, which act as "lego-like" blocks of neocartilage, are capable of assembling into human cartilage with physiologic-like structure and mechanical properties.

According to various embodiments of the present disclosure, signals for cell differentiation and early cartilage development are provided to the cell milieu to engineer mechanically functional human cartilage. In some embodiments, a cellular self-assembly method is provided that mimics mesenchymal condensation, a pivotal stage in the development of skeletal and other mesenchymal tissues that is mediated by cell adhesion molecules and extracellular matrix (ECM). During physiologic condensation, cells can form dense cellular bodies that undergo a series of mesenchymal condensation stages. The mesenchymal condensation sets boundaries that can define the subsequent growth and differentiation of cellular bodies. In vitro, mesenchymal stem cells are shown to undergo cellular condensation and chondrogenesis in the presence of regulatory factors such as TGF-ß.

According to various embodiments, the mesenchymal stem cell condensation is provided as a method to engineer functional human cartilage. Condensed mesenchymal cell bodies (CMBs) can be induced to form large homogenous cell aggregates by fusing before the setting of their condensation boundaries. This method may generate centimeter-sized, anatomically shaped articular cartilage constructs with physiologic stratification, stiffness, and tribological properties. The ability of CMBs to repair cartilage is shown in an in vitro cartilage-defect model. This approach may be used for regenerative medicine; not only in the context of cartilage, but also for other tissues originating from mesenchymal condensation.

As described herein, recapitulation of some aspects of mesenchymal condensation have led to the formation of functional cartilage from hMSCs. Referring to FIGS. 1 to 6, hMSC condensation and boundary setting were investigated in vitro. As illustrated, in one embodiment, hMSCs underwent condensation into CMBs within 1 day, with boundaries setting as early as 7 days post-aggregation.

Developmental studies show that tenascin-C and syndecan-3, key boundary setting proteins during mesenchymal condensation, are highly expressed at the periphery of the developing chick limb outlining humerus, radius, and ulna.

Only early stage CMBs (<7 days), before the setting of a boundary, could be homogenously fused and induced into chondrogenic differentiation and the formation of large and functional cartilage tissues. These findings are consistent with the reported role of tenascin-C in modulating cell attachment to fibronectin.

According to various embodiments of the present disclosure, large cartilaginous tissues with physiologic compressive modulus and lubricative property are successfully engineered in vitro by fusing CMBs and inducing their chondrogenic differentiation while also establishing an interface with subchondral bone as shown in FIGS. 7-10.

Figure 2:
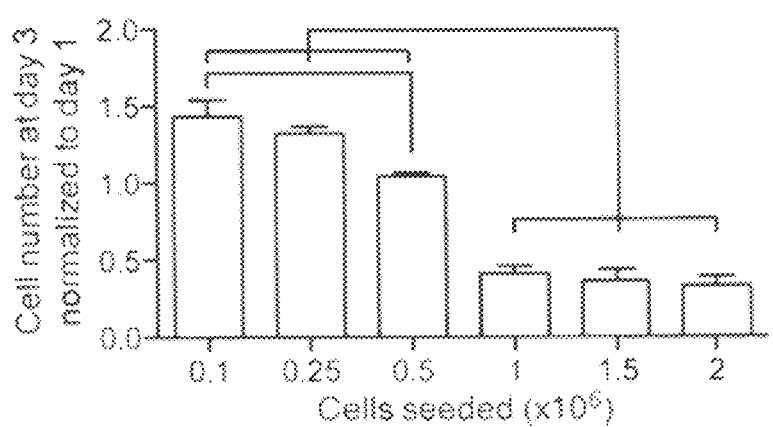
FIG. 2 depicts one embodiment where the DNA content in a condensed cellular body quantified and normalized to the initial seeding DNA content, showing that the efficiency of aggregation decreases as the cell numbers increase.

In one embodiment, hMSCs were suspended in medium supplemented with TGF-ß3 and allowed to aggregate at the bottom of a well, condensed into a single cellular body after 12 hours of incubation. By day 3, small aggregates (containing <5×10$^5$ cells) formed dense spherical cellular bodies in contrast to the larger aggregates (containing 5×10$^5$ to 2×10$^6$ cells) that formed biconcave disk structures indicative of inadequate condensation as indicated in FIG. 1. FIG. 2 shows that the relative increase in the cellularity was also higher for the small than for the large aggregates. 2.5×10$^5$ cells were selected for the formation of CMBs.

Figure 4:
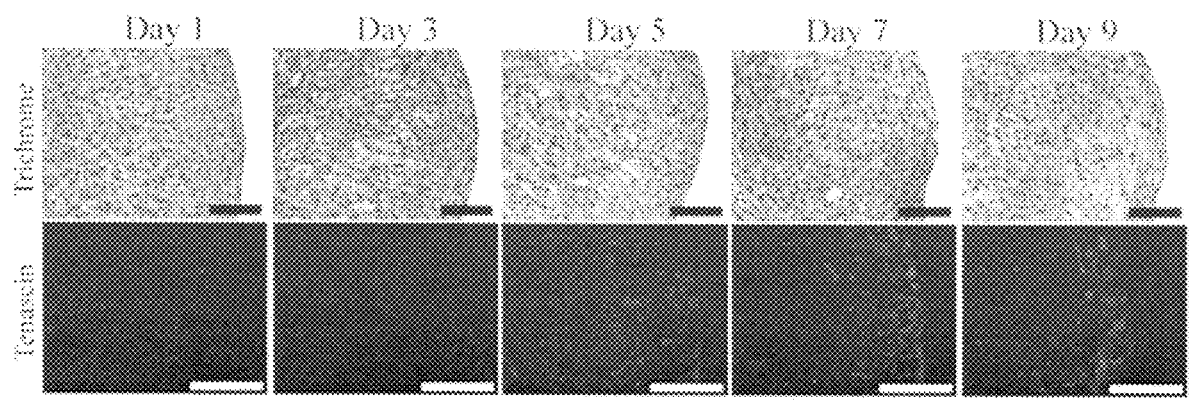
FIG. 4 depicts the tangential cellular lining of CMBs according to some exemplary embodiments of the present disclosure at days 1, 3, 5, 7, and 9 in Trichrome and stained tenascin, an indication of boundary setting (scale bar: 100 μm).
Figure 5:
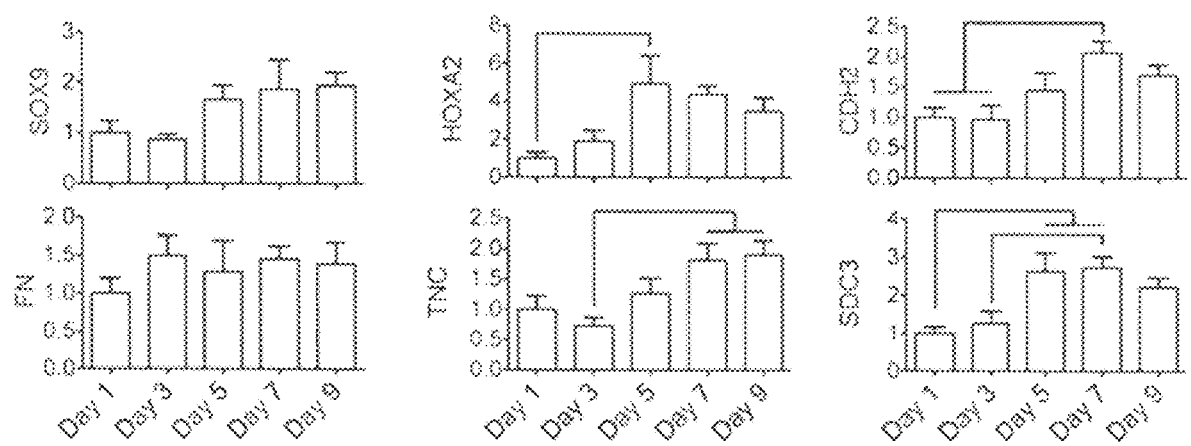
FIG. 5 depicts the characterization of the boundary of CMBs according to embodiments of the present disclosure by high expression of TNC and SDC3 genes, and increased expression of HOXA2 and CDH2 genes. SOX9, chondrogenesis factor, gradually increases as CMBs became more mature. Fibronectin expression, FN, remains constant.

After aggregation, the CMBs developed and maintained their spherical structures over prolonged periods of time. To investigate the formation of tissue boundaries, the production and localization of tenascin was examined, which is a boundary-setting protein in mesenchymal condensation. The production of tenascin increased over time, such that by day 7 of condensation, a tenascin-rich ECM was present on the entire outer surface of the CMB, setting a boundary for advanced stages of condensation (FIG. 4). The expression of fibronectin (FNI) remained stable, whereas the expression of chondrogenic differentiation factor sex determining region Y (SRY)-box 9 (SOX9), transcription factor for cell adhesion homeobox A2 (HOXA2), cell adhesion cadherin 2 (CDH2) gene, and boundary setting proteins tenascin C (TNC) and syndecan 3 (SDC3) all increased with time (FIG. 5), providing evidence for maturation of the condensation process and setting of the mesenchymal condensation boundaries.

Figure 3:
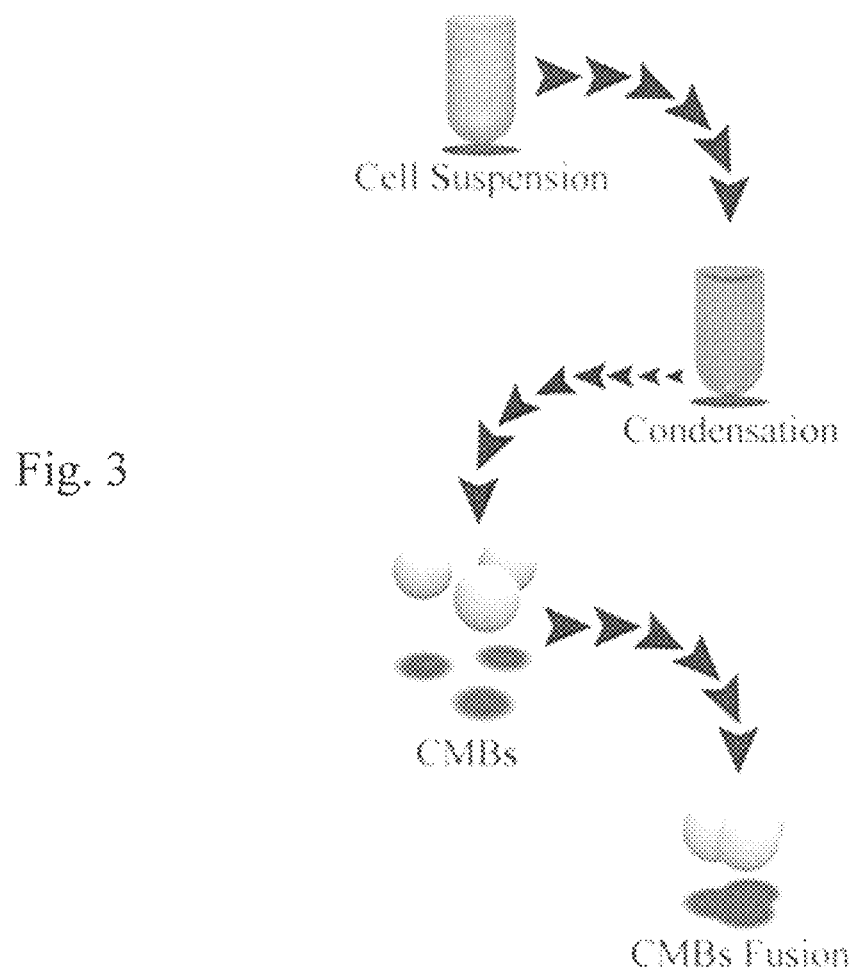
FIG. 3 is a schematic illustration of the condensation and fusion of CMBs according to an exemplary embodiment of the present disclosure.
Figure 6:
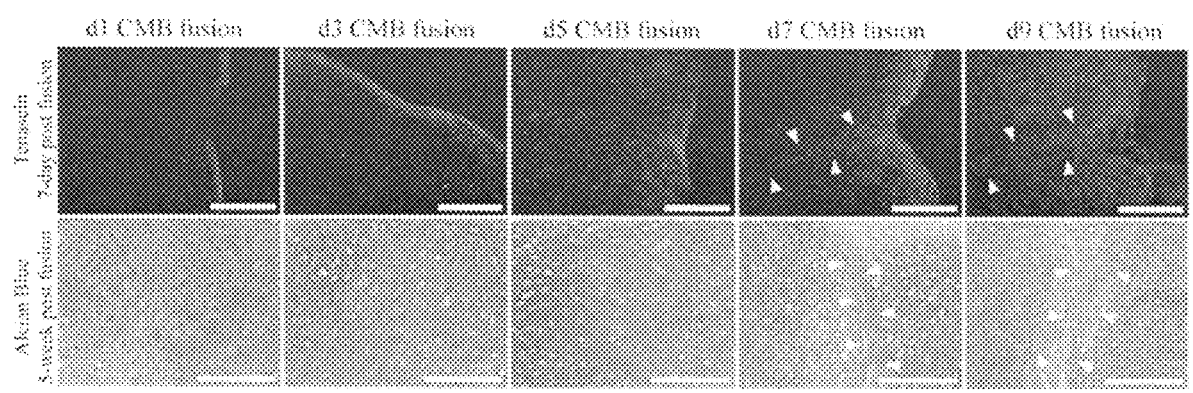
FIG. 6 depicts fusion of CMBs according to embodiments of the present disclosure at different developmental stages (scale bar: 200 μm). At days 7-9 post-fusion, all CMBs show tenascin deposition (Upper Row) at the periphery, in contrast to early stage CMBs (d 1-5). Chondrogenesis in fused early stage CMBs resulted in a homogenous glycosaminoglycan structure (Lower Row), whereas the border between the adjacent CMBs was clearly seen in fused late stage CMBs (arrow).

The CMBs developed a boundary within 7-9 days of culture, and their ability to homogenously fuse with one another at various developmental stages was investigated (FIG. 3). At 7 days postfusion, tenascin was present at the outer surfaces of CMBs and between adjacent CMBs, suggesting insufficient integration (FIG. 6). The set boundary around maturing CMBs (7-9 days) resulted in a well-established border around tissue bodies that was maintained over 5 week of chondrogenic differentiation (FIG. 6). In contrast, homogenous integration was achieved when early stage CMBs (1-5 days of condensation) were fused together (FIG. 6).

Figure 7:
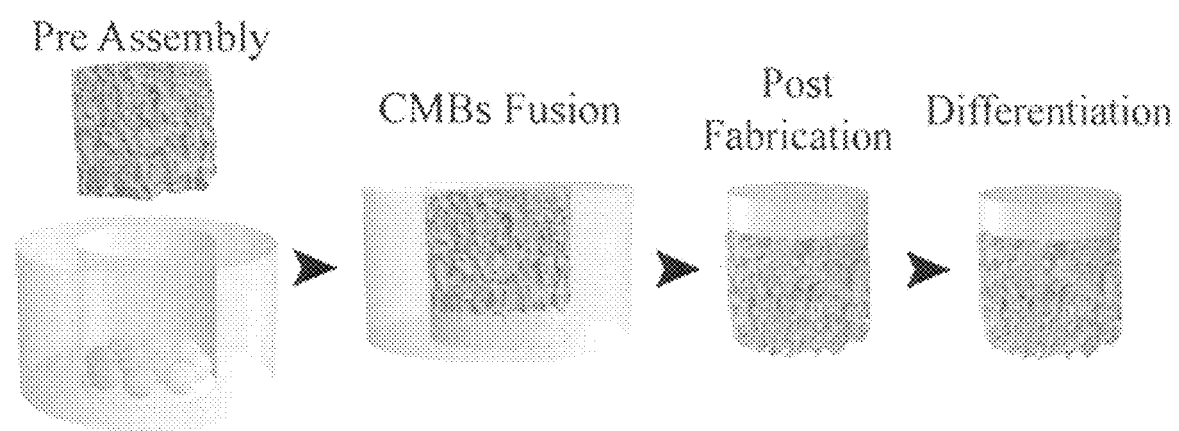
FIG. 7 depicts a method of forming articular cartilage on bone substrate according to embodiments of the present disclosure, in which CMBs are placed into a PDMS ring, a bone scaffold is inserted and pressed onto CMBs to cause CMBs to fuse and penetrate inside the scaffold pores resulting in a composite osteochondral construct. After differentiation, the cellular layer is formed into cartilage and integrated with the porous scaffold.
Figure 8:
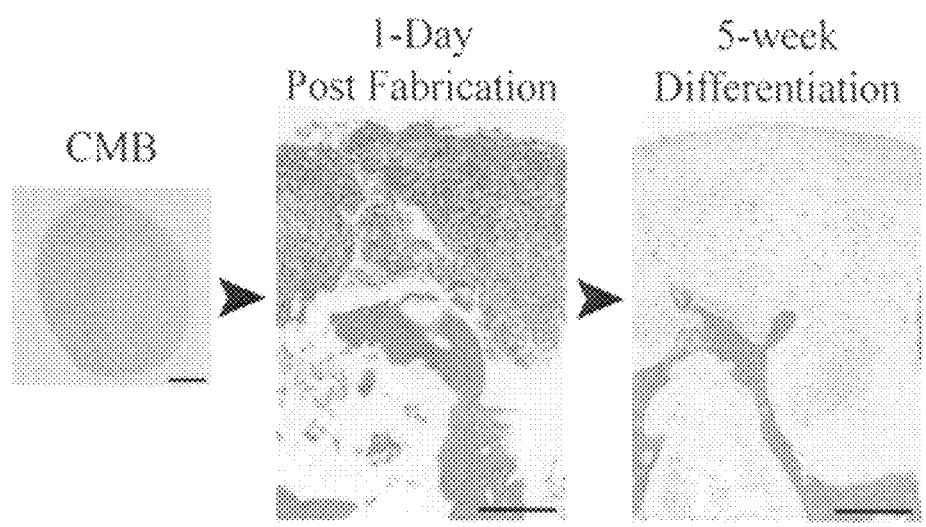
FIG. 8 depicts CMBs and osteochondral constructs according to embodiments of the present disclosure at d 1 and week 5 post-fusion, in which histological and immunohistochemical sections of the bioengineered cartilage and subchondral bone indicate appropriate matrix composition and cartilage formation.
Figure 9:
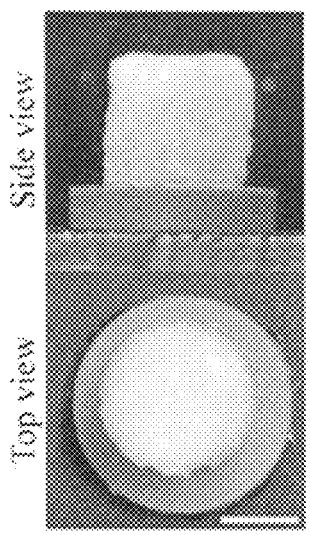
FIG. 9 depicts top and side views of the articular cartilage plug with the fused CMBs developed into thick cartilage layer covering the whole construct surface according to embodiments of the present disclosure.
Figure 10:
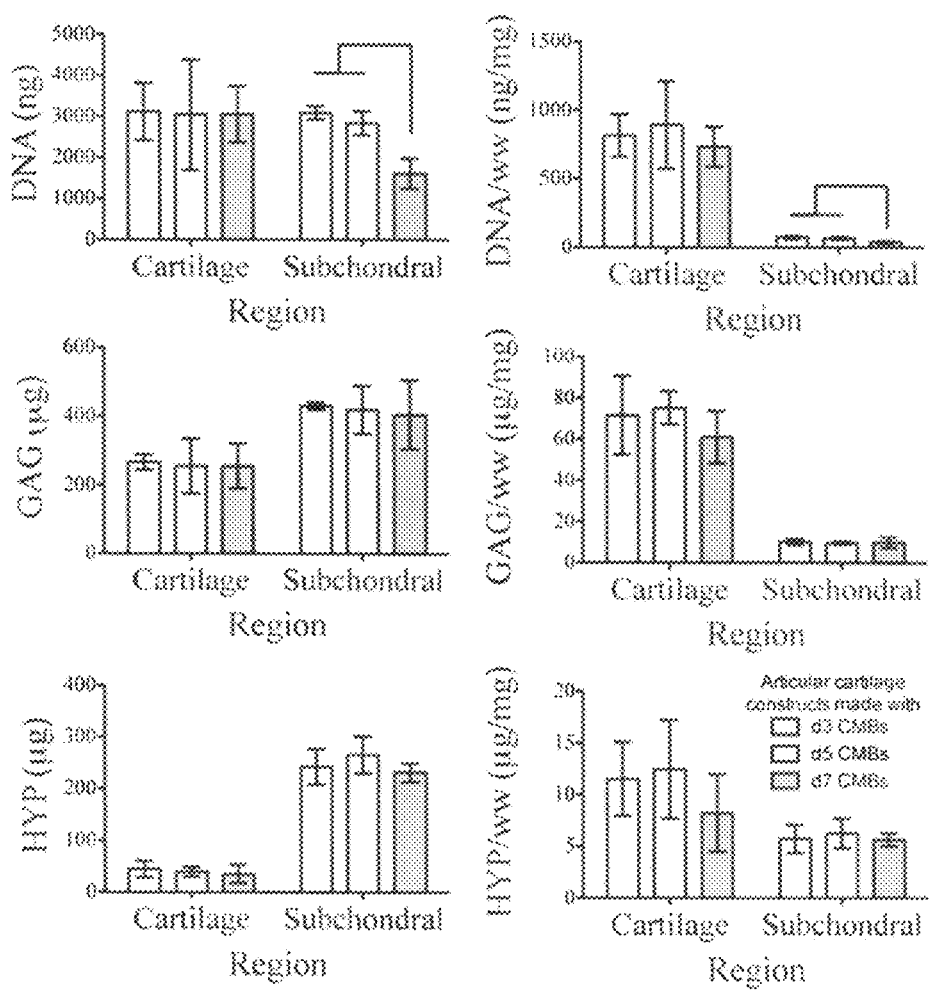
FIG. 10 illustrated the contents of DNA, glycosaminoglycan (GAG), and hydroxyproline (HYP) of cartilage layers created from d3, d5, and d7 CMBs according to embodiments of the present disclosure after 5 wk of chondrogenic induction. Subchondral regions had similar GAG and HYP contents, and significantly lower DNA content for d7 CMBs, suggesting reduced migratory and integrative ability.

Referring to FIGS. 7 and 8, a medical device comprising functional cartilage generated from fused CMBs was prepared. In this exemplary embodiment, a layer of CMBs was attached to porous decellularized bone matrix. A dense cellular region was generated (a precursor of articular cartilage) and penetration of CMBs into the bone matrix was facilitated (a precursor of the subchondral region). The dense cellular layer developed into cartilage and integrated with the bone matrix over 5 weeks of cultivation (FIGS. 8 and 9). It was observed that cells within early stage CMBs (1-5 days) were more penetrative and migratory than the cells in later stage CMBs (7 days), as measured by the cellular content of the subchondral region (FIG. 4). Chondrogenic differentiation capabilities of fused CMB at different stages of maturity were similar, as indicated by the amounts of glycosaminoglycan and hydroxyproline (FIG. 4). Referring to Table 1, the resulting mechanical properties of the articular cartilage tissues were significantly different. The Young's modulus of cartilage was significantly higher for the early stage CMBs than the late stage CMBs. There was no significant difference with the corresponding friction coefficients. Notably, the Young's modulus (averaging greater than 800 kPa, Table 1) and equilibrium friction coefficient (0.28, Table 1 and FIG. 1-2) of cartilage engineered from early stage CMBs over 5 week in vitro were in the physiological ranges for adult human articular cartilage.

TABLE 1

Mechanical properties of human cartilage engineered by CMEfusion

| Articular cartilage constructs | Young's modulus, kPa | Minimum friction coefficient, $\mu_{min}$ | Equilibrium friction coefficient, $\mu_{max}$ |
| --- | --- | --- | --- |
| Day 3 CMBs | 788 ± 200 | 0.049 ± 0.008 | 0.276 ± 0.033 |
| Day 5 CMBs | 825 ± 197 | 0.046 ± 0.010 | 0.283 ± 0.042 |
| Day 7 CMBs | 457 ± 46* | 0.064 ± 0.013 | 0.334 ± 0.053 |

*Statistically different from the other groups (P < 0.05).

Figure 12:
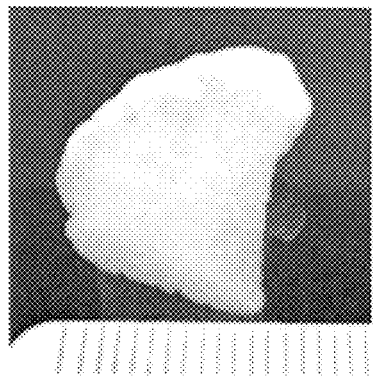
FIG. 12 depicts an anatomical layer of articular cartilage on underlying bone after 5 wk of cultivation according to embodiments of the present disclosure.
Figure 13:
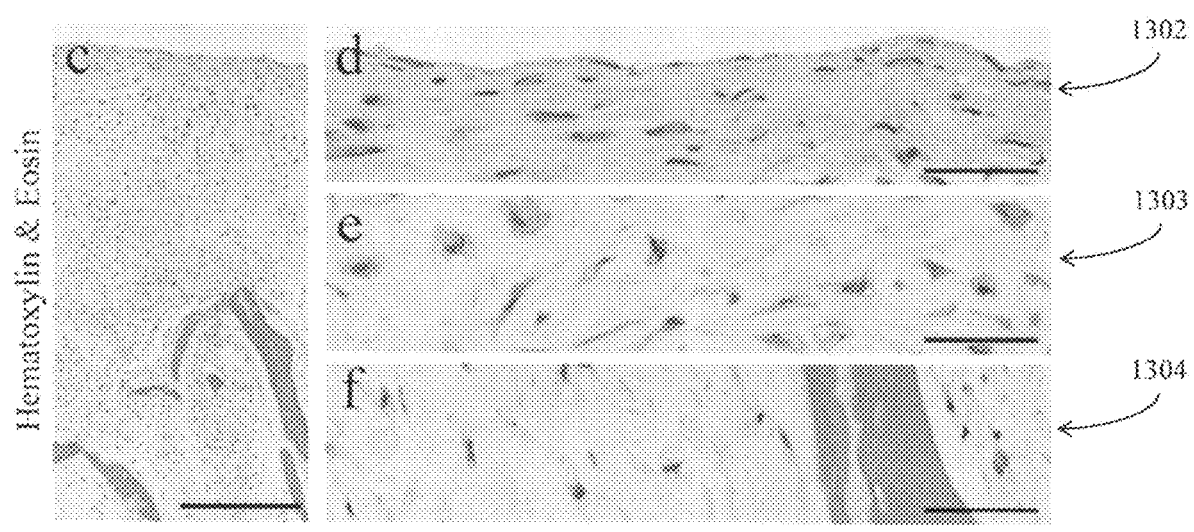
FIG. 13 depicts histological and immunohistochemical analysis of cartilage matrix according to embodiments of the present disclosure stained for H&E (Scale bar: 500 μm in low-magnification images and 50 μm in high-magnification images).
Figure 14:
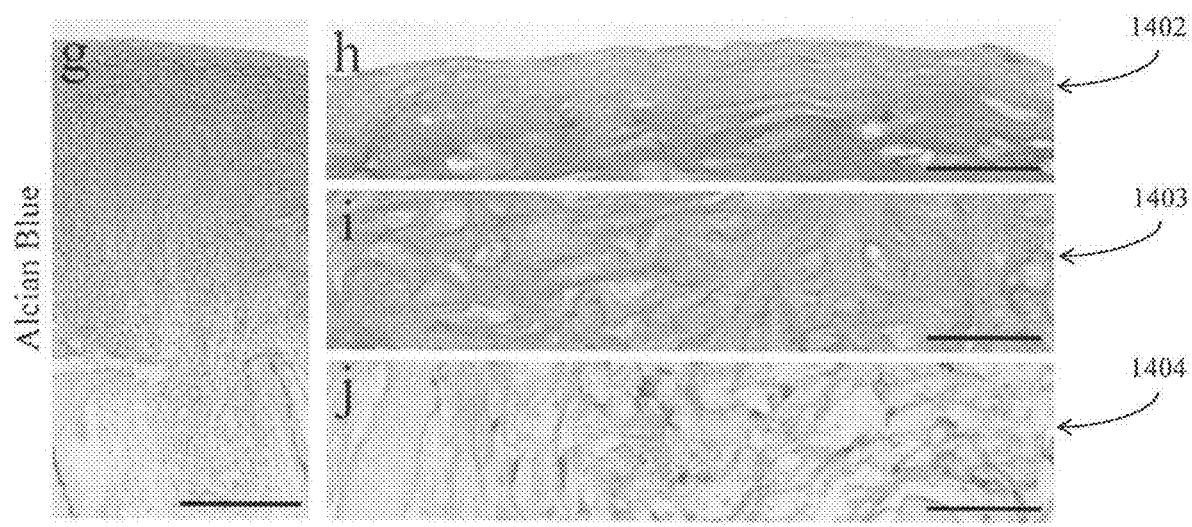
FIG. 14 depicts histological and immunohistochemical analysis of cartilage matrix according to embodiments of the present disclosure stained for Alcian blue for GAG (Scale bar: 500 μm in low-magnification images and 50 μm in high-magnification images).
Figure 15:
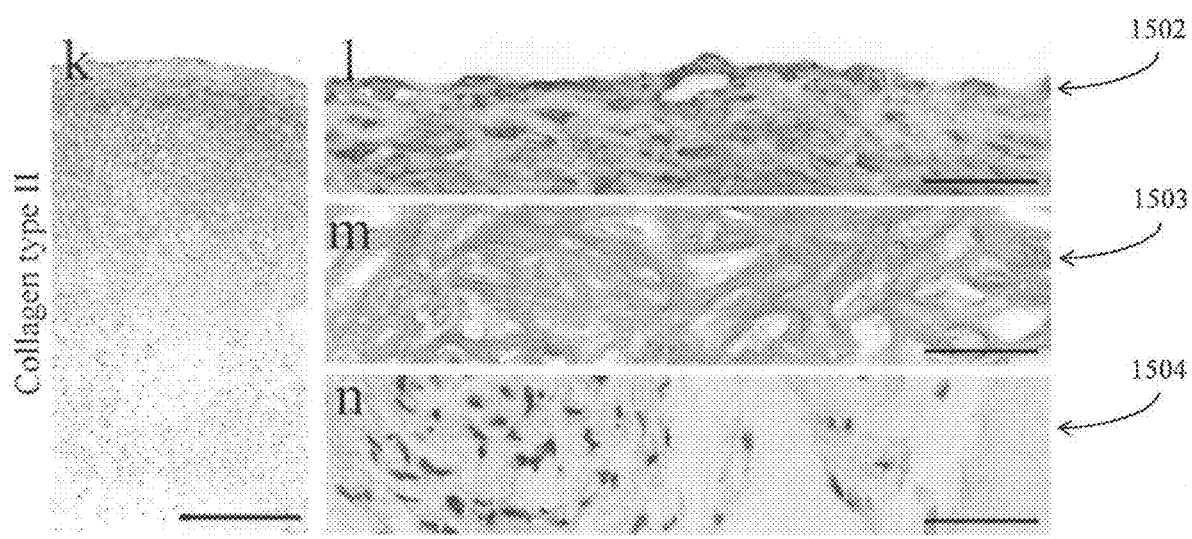
FIG. 15 depicts histological and immunohistochemical analysis of cartilage matrix according to embodiments of the present disclosure stained for anticollagen type II (Scale bar: 500 μm in low-magnification images and 50 μm in high-magnification images).
Figure 16:
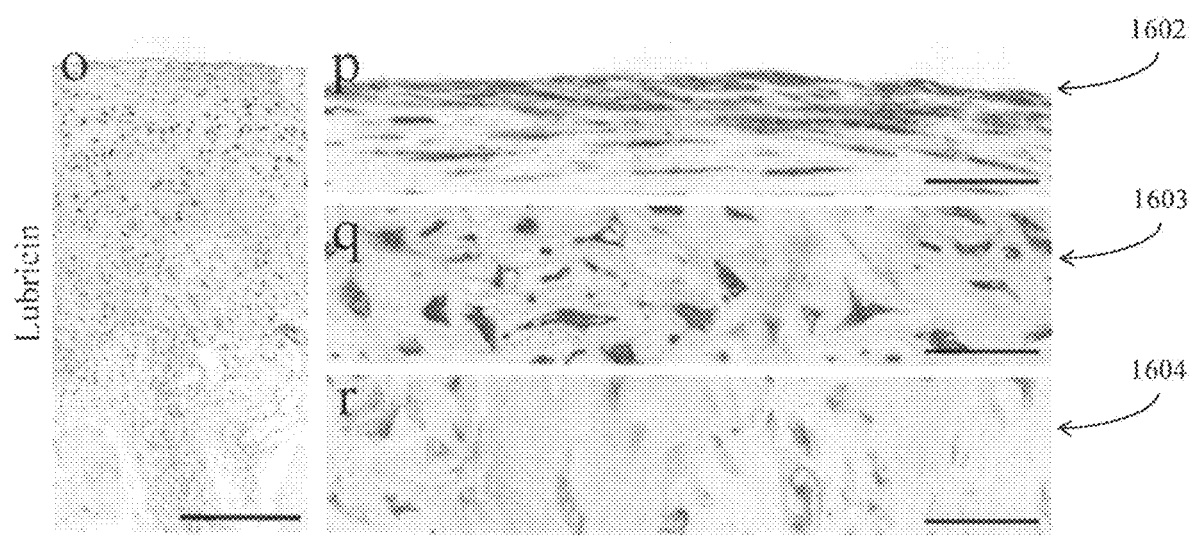
FIG. 16 depicts histological and immunohistochemical analysis of cartilage matrix according to embodiments of the present disclosure stained for anti-lubricin (Scale bar: 500 μm in low-magnification images and 50 μm in high-magnification images).
Figure 17:
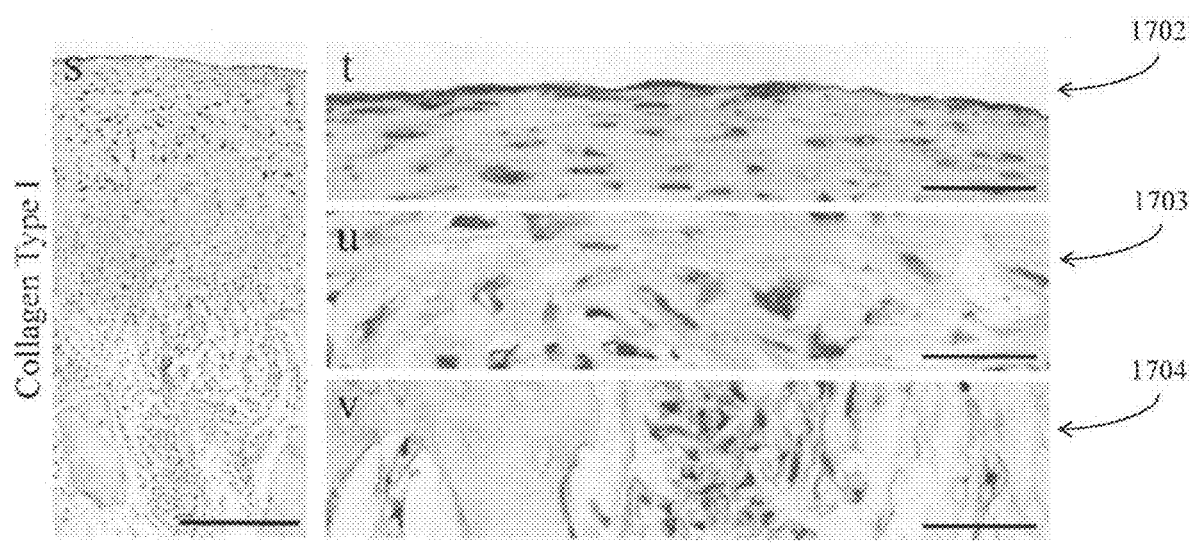
FIG. 17 depicts histological and immunohistochemical analysis of cartilage matrix according to embodiments of the present disclosure stained for anticollagen type I (Scale bar: 500 μm in low-magnification images and 50 μm in high-magnification images).
Figure 18:
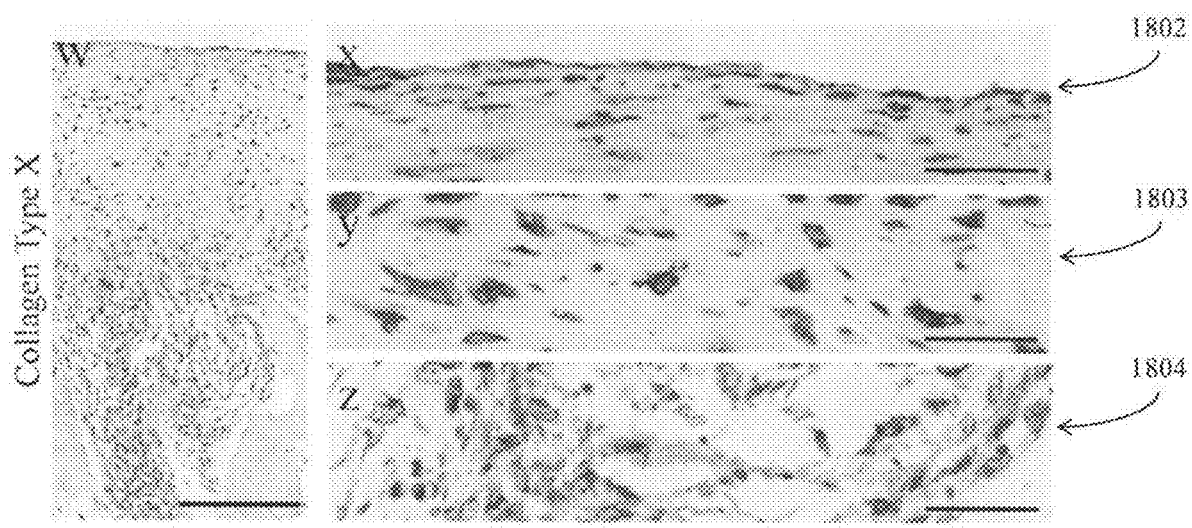
FIG. 18 depicts histological and immunohistochemical analysis of cartilage matrix according to embodiments of the present disclosure stained for anticollagen type X (Scale bar: 500 μm in low-magnification images and 50 μm in high-magnification images).

In another embodiment, anatomically shaped cartilage was grown in vitro. In this embodiment, the condylar cartilage was engineered by press-molding CMBs onto anatomically shaped porous bone scaffolds (FIG. 1). The CMBs formed a dense cellular layer penetrating into the scaffold and developed into a thick cartilage layer (>1 mm) covering the condylar surface of the scaffold after 5 wk of cultivation (FIG. 12). Histological analysis revealed physiologic-like articular cartilage tissue structure (FIG. 13-18). The cartilaginous ECM contained high amounts of glycosaminoglycan and collagen type II (FIG. 14-15). In the deep zone (1303, 1403, 1503, 1603, 1703, 1803), cells were found in lacunae surrounded by ECM rich in glycosaminoglycan (1403) and collagen type II (1503). The superficial zone (1302, 1402, 1502, 1602, 1702, 1802) consisted of flat cells and lubricin-rich ECM arranged tangentially to the articular surface (1602). In the subchondral region, ECM was composed of glycosaminoglycan, collagen type I, and collagen type X (1304, 1404, 1504, 1604, 1704, 1804).

Figure 20:
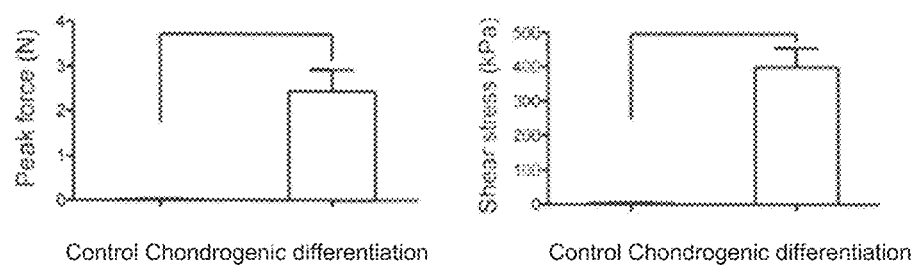
FIG. 20 illustrates the integration between native cartilage and CMBs formed cartilage tissue according to embodiments of the present disclosure after 5 wk of chondrogenic induction through measured peak force and shear stress needed to break the integration surface.
Figure 21:
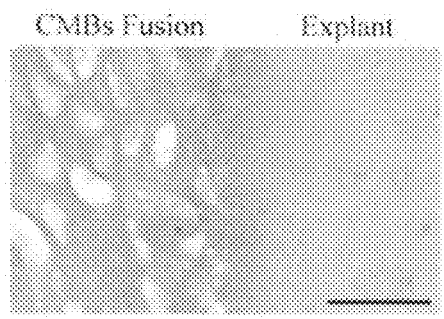
FIG. 21 illustrates the high integration strength achieved by embodiments of the present disclosure due to the structural integration of glycosaminoglycan and collagen type II as indicated by Alcian blue (Scale bar: 50 μm).
Figure 22:
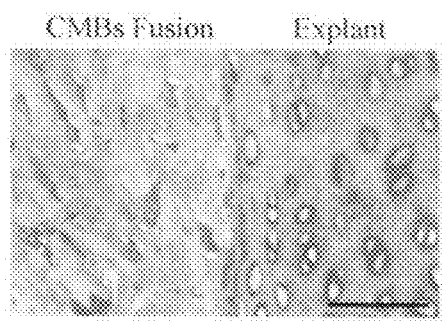
FIG. 22 illustrates the high integration strength achieved by embodiments of the present disclosure due to the structural integration of glycosaminoglycan and collagen type II as indicated by anticollagen type II immunohistochemistry stain (Scale bar: 50 μm).

In one aspect, cartilage repair by CMBs in an in vitro model is provided. Using an in vitro model of cartilage defect similar to those used before, we evaluated the capacity of CMBs for cartilage regeneration. The fused CMBs completely filled the cartilage defect and integrated with the surrounding cartilage after 5 weeks of cultivation under chondrogenic conditions. The integration strength was determined by the force and stress required to break the integration interface between the fused CMBs and the surrounding cartilage. Both the force and the stress were two orders of magnitude higher in the CMB group than in untreated control defects (2.5±0.48 N vs. 0.03±0.02 N; 399±56 kPa vs. 4.4±1.9 kPa, respectively) (FIG. 20). The high integration strength correlated to the formation of cartilaginous ECM by fused CMBs (FIG. 21-22).

Unlike previously proposed scaffold-based or self-aggregating techniques for cartilage tissue engineering, the methods of the present disclosure mimic mesenchymal condensation in tightly packed cellular aggregates that eventually develop into well-stratified cartilage interfaced with underlying bone. The compressive modulus and friction coefficient measured for engineered cartilage after 5 wk of cultivation are within the range of values measured for native articular cartilage. Although the total collagen content is lower than the native cartilage, the resulting compressive modulus was associated with the high density of GAG (FIG. 7-10), similarly to the results with engineered cartilage from chondrocytes. The fusion of CMBs before the setting of condensation boundaries was essential for the formation of functional cartilage constructs and their seamless integration with the underlying bone. Such biological fidelity has not been accomplished thus far by any method of cartilage formation from hMSCs.

By using the free-forming property of early stage CMBs, a continuous 1-mm thick cartilage layer is engineered covering the condylar surface of anatomical decellularized bone scaffold, with a composition, structure, and mechanical and surface properties resembling native articular cartilage (FIG. 11-18). The stratified formation of superficial surface with its lubricin-rich layer (FIG. 16) was associated with a physiologically low friction coefficient of the cartilaginous surface (Table 1). Furthermore, the presence of collagen type X at the interface between the cartilage layer and the subchondral region (FIG. 18) suggested the development of calcified cartilage. GAG density near the bone interface within large constructs was lower than in the native cartilage-bone interface, which is rich in both collagen type X and GAG, suggesting the need for differentiation toward a more hypertrophic chondrocyte lineage or a longer culture time. Further studies will also need to confirm that the cartilage based on CMBs remains patent if challenged by in vitro hypertrophic regimens and following implantation into a joint.

The utility of fusing CMBs was further examined using an in vitro cartilage-defect model (FIG. 19-22). Following chondrogenic induction, the fused CMBs filled the defect and mechanically and structurally integrated with the surrounding native cartilage. This ability for integration holds promise that CMBs could be clinically applied to repair defects by simple injection delivery similarly to the chondrospheres system.

According to various embodiments of the present disclosure, mechanically functional human cartilage interfaced with subchondral bone substrate can be grown in vitro by mimicking some aspects of the pivotal developmental process of mesenchymal condensation. This technique results in clinically sized and anatomically shaped human cartilage with physiological stratification, Young's moduli (>800 kPA), and friction coefficients (<0.3). The same technique can be used for repairing defects in native articular cartilage, as evidenced by the formation of cartilage-cartilage interface with integration strengths of 400 kPa. The same technique can be extended to bioengineer other tissues, such as tendon or meniscus, and to the use of other cell sources, such as embryonic and induced pluripotent stem cells.

EXAMPLES

Bone Marrow Derived Human Mesenchymal Stem Cells

Fresh human bone marrow aspirates were obtained from Cambrex. The bone marrow-derived human mesenchymal stem cells (hMSCs) were isolated by their attachment to the plastic surfaces. Cells were expanded in DMEM supplemented with 10% FBS, 1% pen-strep, and 0.1 ng/mL basic fibroblast growth factor. The hMSCs were cultured up to the third passage and were shown to exhibit multi-lineage differentiation capability.

Generation of Condensed Mesenchymal Bodies (CMB)

hMSCs were suspended in cultured medium (high-glucose DMEM supplemented with 100 nM dexamethasone, 50 µg/ml ascorbic acid-2-phosphate, 100 µg/ml sodium pyruvate, 40 µg/ml praline, 1% insulin, transferrin, sodium selenite [ITS+] mix, 1% antibiotics, and 10 ng/ml Transforming Growth Factor-beta3 [TGF-ß3]). To determine the optimal size of CMBs, hMSCs were suspended at concentrations of $10^5$, $2.5 \times 10^5$, $5 \times 10^5$, 106, $1.5 \times 10^6$, and $2 \times 10^6$ cells/ml. 1 ml of cell suspension was added into deep round-bottom 96-well plate (NUNC®, Sigma-Aldrich, MO) and centrifuged at 250 g for 5 min. Cells were incubated in a controlled humidified chamber (37° C., 5% $CO_2$) and media was replaced daily for 3 days. Samples (n=4) were imaged and collected to analyze DNA content. CMBs made using $2.5 \times 10^5$ cells were utilized in all experiments due to their highest ability for condensation (FIG. 1-2).

To examine the CMB maturity, CMBs were incubated in culture medium and were collected every other day starting at day 1 post centrifugation up to 9 days. The CMBs were fixed in 10% formalin or stored in Trizol (n=4). To test CMB fusion capability, three CMBs were pressed inside Polydimethylsiloxane (PDMS) wells (3 mm in diameter and 2 mm deep) at Day 1, 3, 5, 7, and 9 days post centrifugation. The fused CMBs were cultured for an additional 7 days. Fusion of CMBs was investigated histologically in paraffin sections.

Fabrication of Articular Cartilage

Figure 23:
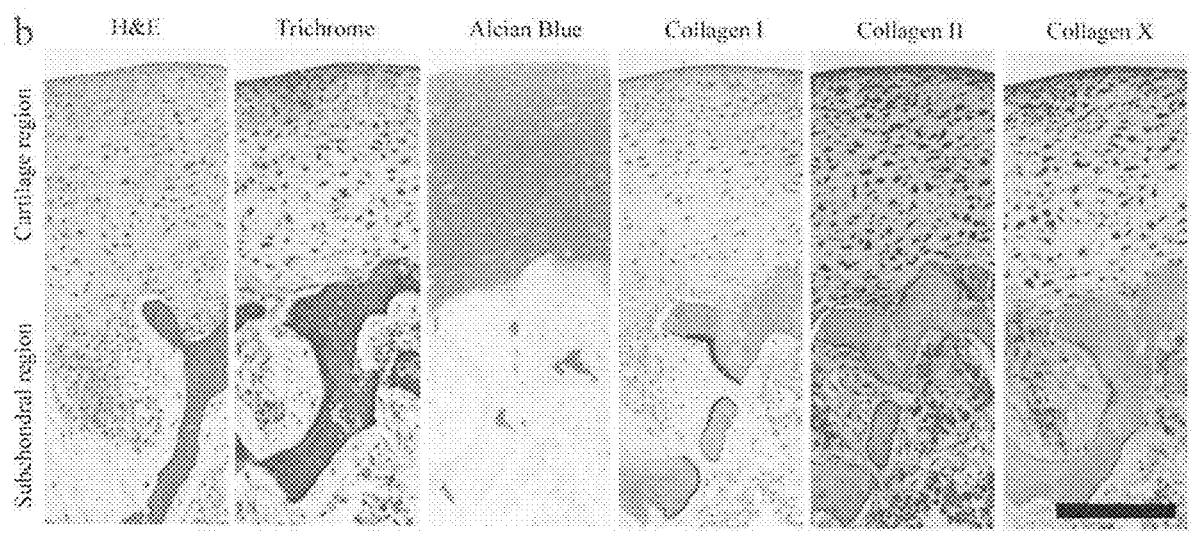
FIG. 23 shows histological and immunohistochemical sections indicating the formation of a well-developed layer of cartilage interfaced with the subchondral bone.
Figure 24:
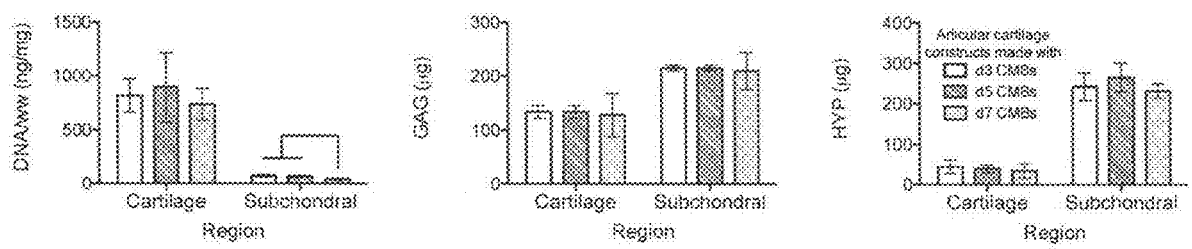
FIG. 24 illustrates biochemical compositions of the cartilage layer and subchondral bone region after 5 weeks of chondrogenic induction in constructs formed using day-3, day-5, and day-7 CMBs. In the cartilage layer, DNA, GAG, and hydroxyproline (HYP) contents were comparable across different groups. In the bone region, DNA content was significantly lower in constructs made from d7 CMBs suggesting that the more mature CMBs exhibit less migratory and integrative ability.
Figure 25:
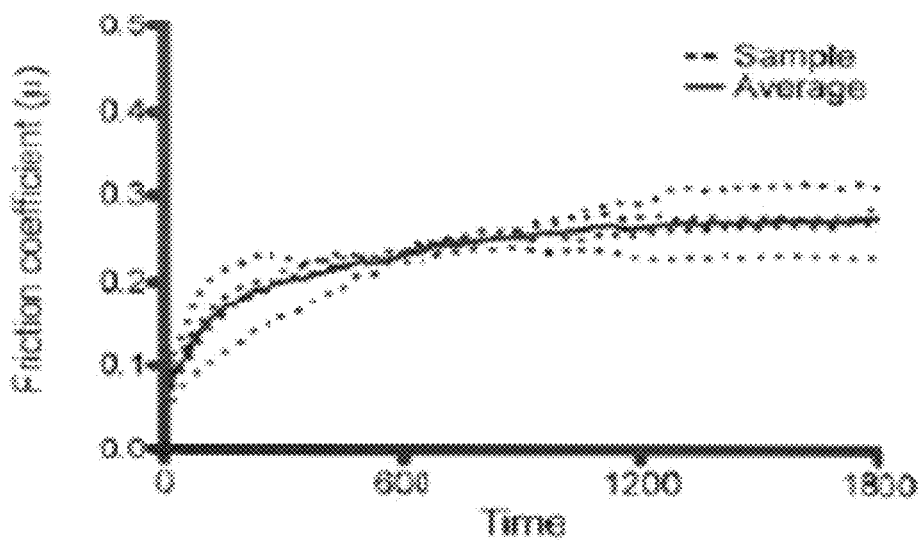
FIG. 25 illustrates tribological properties of bioengineered cartilage. Friction coefficients (μ) measured for articular cartilage made using day-3, day-5, and day-7 CMBs were in the range of values for adult human articular cartilage, and increased with the time of loading, a behavior indicative of viscoelastic properties of cartilage. μmin:the initial μ at the start of the test; μeq: the equilibrium μ value after 1800 seconds of testing.
Figure 25:
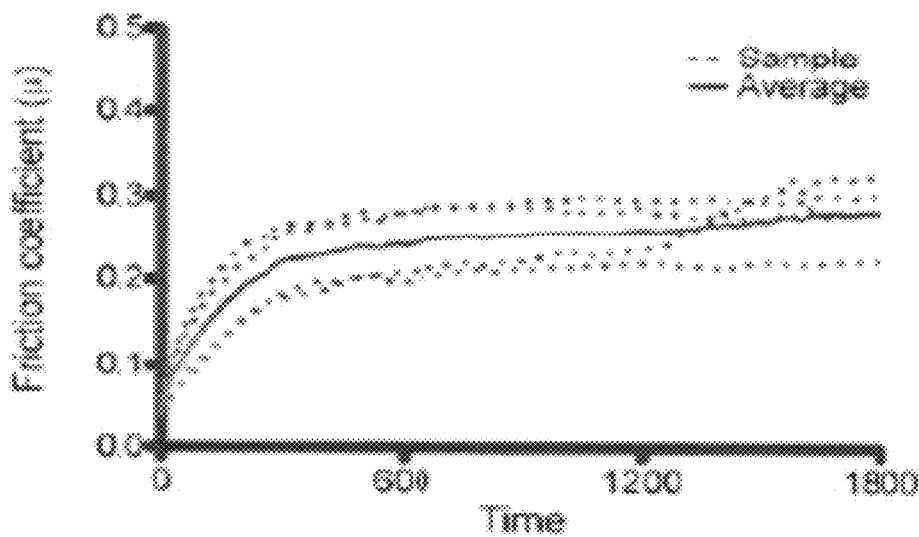
Figure 25:
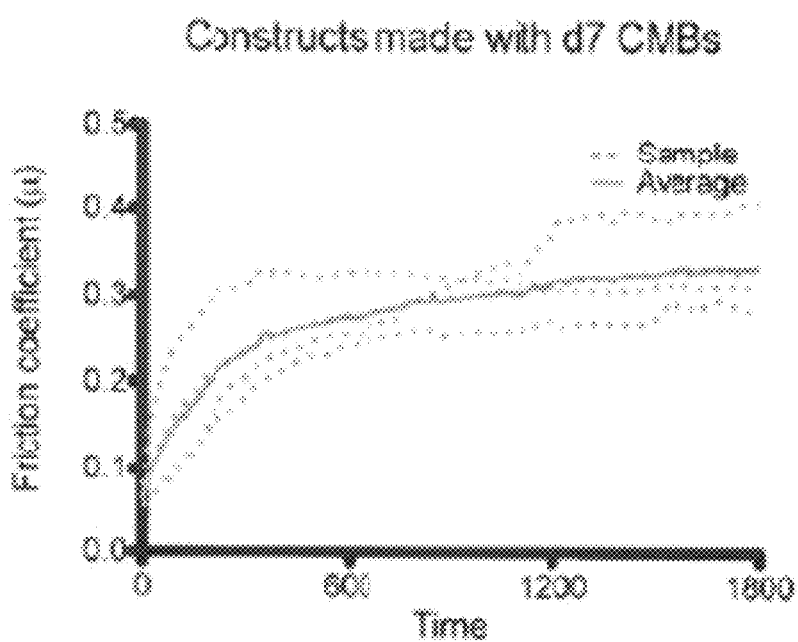
Figure 26:
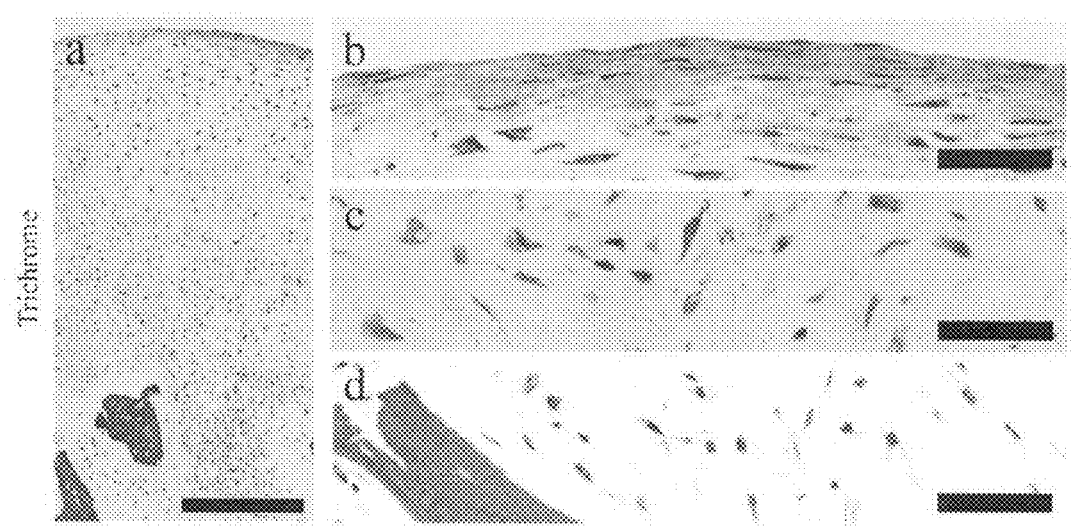
FIG. 26 illustrates the organization of the cartilaginous matrix in osteochondral constructs in Trichrome stain. The overall cross-section of the cartilage layer is shown at the left; high magnifications of the surface, middle and deep layers are shown at the right. Collagen type I and Collagen type X are highly expressed in the subchondral region (d) and only minimally in the superficial region (b) and deep cartilage region (c). Scale bars: (a) 500 μm; (b-d) 50 μm.

To fabricate cylindrical articular cartilage, eight CMBs (day 3, 5, or 7) were placed in a PDMS ring with inner diameter of 4 mm×4.5 mm thick. Decellularized trabecular bone matrix scaffolds (4 mm in diameter×4 mm thick) 2 were pressed inside the ring on top of the CMBs. The CMBs fused together and penetrated inside the porous scaffold resulting in constructs with cell layer of 500 µm thick over the scaffold (cartilage region) and penetrated into the subchondral region (FIG. 22-23). The constructs were cultured for 5 weeks and analyzed mechanically (n=4), biochemically (n=4), and histologically.

To fabricate anatomical articular cartilage, a 3D image of a human condyle was obtained from CT scans taken from a patient (according to an active IRB, with fully de-identified images). A 1-mm thick cartilage region was created over the articular surface of the condyle. A PDMS mold was fabricated from the 3D printed condyle with cartilage layer and cut into two pieces: one to hold the scaffold and the other to hold the articular cartilage side for pressed molding of CMBs. Day-3 CMBs (n=120) were placed inside the mold at the articular cartilage side. Anatomical human condyle scaffolds created from decellularized trabecular bone, as previously described, were fitted inside the PDMS mold and lowered onto the articular cartilage side of the PDMS mold to fuse the CMBs and guide cell penetration into the scaffold. The constructs were cultured in 10 ml of medium for 5 weeks with medium changes twice per week.

RT-PCR RNA was purified according to the manufacturer's instructions using the Trizol method. Mesenchymal condensation transcriptional factors (SOX9 and HOXA2), cell adhesion gene (CDH2), and condensation extracellular matrix genes (FNl, TNC, and SDC3) were quantified using real-time PCR machine with TaqMan® primers (Life Technologies™, CA):

TABLE 2

| Gene | TaqMan ® Primer |
| --- | --- |
| GAPDH | Hs02758991_g1 |
| SOX9 | Hs01001343_g1 |
| HOXA2 | Hs00534579_m1 |
| CDH2 | Hs00983056_m1 |

TABLE 2-continued

| Gene | TaqMan ® Primer |
|---|---|
| FN1 | Hs00365052_ml |
| TNC | Hs01115665_ml |
| SDC3 | Hs01568665_ml |

Immunofluorescence and immunohistochemical staining after fixation, samples were decalcified with Immunocal solution (if containing decellularized bone scaffold), paraffin embedded and cut into 5 µm thick sections. The sections were stained with haematoxylin and eosin (H&E), Alcian Blue for GAG and trichrome. Samples were also immunohistochemically stained for collagens I, II, X, and lubricin (Abcam, MA). N-Cadherin and Tenascin antibody (Millipore, MA) were utilized for immunofluorescence staining.

Biochemical analysis DNA, GAG and hydroxyproline contents were measured as previously described. In brief, the cartilage and subchondral regions were separated along the flat surface of the porous decellularized bone scaffold and wet weights were determined. The samples (n=4 per group) were digested in 0.5 ml proteinase K solution at 50° C. DNA content was determined using the Picogreen assay (Molecular Probes, OR). The sulfated GAG (s-GAG) content of the extract was determined using the 1,9-dimethylmethylene blue (DMMB) dye calorimetric assay with chondroitin-6-sulfate as a standard. Hydroxyproline content was measured by acid hydrolysis. Mechanical testing of articular cartilage the compressive Young's modulus of the cartilage was measured in PBS using unconfined compression as previously described. The cylindrical constructs were compressed at 0.01% strain/s for up to 3,000 seconds and the compressive load was measured. Young's modulus was calculated from the linear slope of the stress-strain curve.

Friction coefficient between the cartilage and glass was measured in PBS bath in unconfined compression as previously described. Continuous reciprocal sliding was utilized at a velocity of 1 mm/s and translational range of ±10 mm. The normal force, frictional force and axial deformation of the cartilage were monitored throughout the test. All tests were terminated after 1,800 seconds. The time-dependent friction coefficient, $\mu eff$, was calculated from the ratio of the friction force to the normal force. The minimum friction coefficient, $\mu min$, and the equilibrium friction coefficient, $\mu eq$, represented the minimum value of $\mu eff$ and the value achieved at the end of the run, respectively.

Statistical analysis Pair-wise comparisons of results were carried out using multi-way Analysis of Variance (ANOVA) followed by Turkey's multiple comparison test using Prism software with a of 0.05.

Generation and Fusion of CMBs.

To generate CMBs, hMSCs were suspended in chondrogenic medium (high glucose DMEM supplemented with 10 ng/mL TGF-133, 100 nM dexamethasone, 50 µg/mL ascorbic acid-2-phosphate, 100 µg/mL sodium pyruvate, 40 µg/mL proline, 1% insulin, transferrin, sodium selenite (ITS)+mix, and 1% penicillin-streptomycin). To determine the optimal size of CMBs, hMSCs were suspended at the concentrations of $10^5$, $2.5 \times 10^5$, $5 \times 10^5$, $10^6$, $1.5 \times 10^6$, and $2 \times 10^6$ cells/mL. One milliliter of cell suspension was aliquoted into deep round-bottom 96-well plates (NUNC; Sigma-Aldrich) and centrifuged at 250×g for 5 min (FIG. 3). Cells were incubated in a controlled humidified chamber [37° C., 5% (vol/vol) CO2] and culture media were replaced daily up to day 3. Samples were imaged and collected to analyze for DNA content (n=4). CMBs formed by using $2.5 \times 10^5$ cells were used in all experiments due to their condensability and the formation of compact spherical CMBs. To investigate the development and maturity of the CMBs, they were incubated in culture medium and collected every other day starting at day 1 post-centrifugation up to 9 days. The CMBs were fixed in 10% (vol/vol) formalin for histological and immunohistochemical analysis or stored in TRizol (n=4) for gene expression analysis. To test the fusion capability of CMBs, three CMBs were pressed with a stainless steel block inside a polydimethylsiloxane (PDMS) wells (3 mm in diameter and 2 mm deep) at days 1, 3, 5, 7, and 9 postcentrifugation (FIG. 3), cultured for up to 5 wk, and evaluated histologically.

Generation of Cylindrical Cartilage Plugs.

Eight CMBs (day 3, 5, or 7) were placed inside a PDMS ring (4 mm inner diameter×4.5 mm high). Decellularized cylindrical trabecular bone matrix scaffolds (4 mm diameter×4 mm high) were processed as previously described and pressed inside the ring on the top of CMBs. Osteochondral constructs were formed by pressing the bone portion into the CMB layer. The internal geometry of the mold, with 0.5 mm of free space for the formation of the cartilage layer, maintained consistency of the applied pressure from one sample to another. A cartilage layer could be formed reproducibly by pressing the CMB layer onto a stainless steel block, but not by spontaneous fusion of CMBs without applying pressure. The constructs were cultured for 5 wk and analyzed mechanically (n=4), biochemically (n=4), and histologically (n=4).

Generation of Anatomically Shaped Cartilage.

Figure 11:
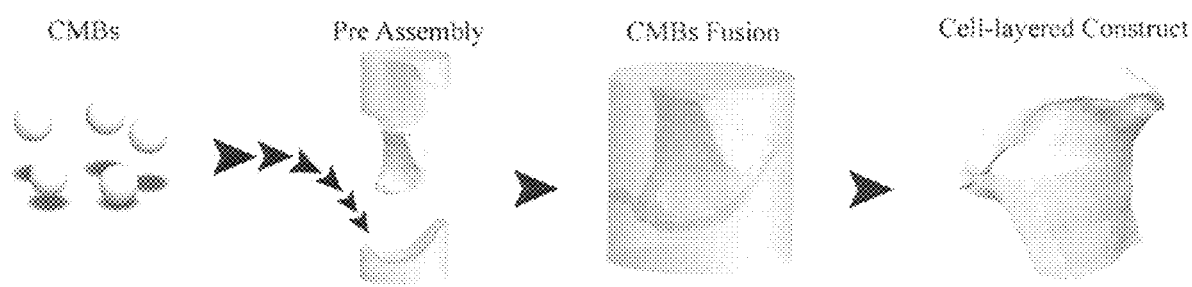
FIG. 11 illustrates a method of CMB fusing according to embodiments of the present disclosure in which CMBs are placed on the cartilage side of a mold in the exact shape of the condyle, an anatomically shaped porous scaffold is placed on the other side, and the two-piece mold is press-fit. CMBs fuse together and adhere to the scaffold as a thick cellular layer along the articular surface.

A 3D image of an anatomical human condyle was obtained from a CT scan of a patient as in our previous studies. A 1-mm thick cartilage region was designed from the reconstructed 3D image to cover the articular surface of the condyle. As for the osteochondral plugs described above, anatomically shaped constructs were formed by pressing the bone portion into the CMB layer, by using a mold providing 1 mm of free space for the formation of the cartilage layer. A PDMS mold was created and cut into two pieces: one to hold the scaffold and the other to contain the articular cartilage side for pressed molding of CMBs (FIG. 11). A total of 120 CMBs (day 3) were placed inside the mold at the articular cartilage side. Anatomical human condyle scaffolds created from decellularized trabecular bone, as previously described, were fitted inside the PDMS mold and lowered onto the articular cartilage side of the PDMS mold to fuse the CMBs and mold them into anatomical shape with cell penetration into the scaffold. The constructs were cultured for 5 wk with medium change twice per week.

Cartilage Defect Model.

Figure 19:
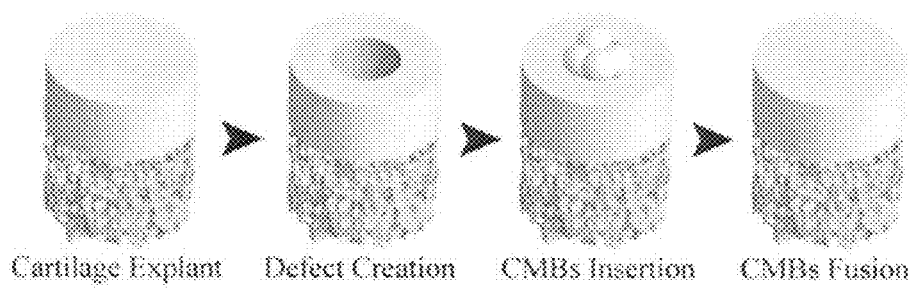
FIG. 19 depicts a method of cartilage repair according to embodiments of the present disclosure in which 1.5 mm diameter cartilage defects are created by biopsy punch and filled with pressed CMBs to fuse and fill the defect.

Osteochondral explants were cored from carpometacarpal joints of 2- to 4-mo-old cows, and cut into cylinders (4 mm in diameter×4-6 mm thick). The cartilage-defect model was created by removing a piece of cartilage at the center of the explant with a 1.5-mm biopsy punch creating a cartilage ring while leaving subchondral bone intact. Four CMBs were placed inside the void cartilage space and packed by pressing with a flat stainless steel block (FIG. 19). The constructs were cultured in chondrogenic media or expansion media (negative control) for 5 wk and analyzed mechanically (n=4) and histologically (n=4).

Fabrication of the Anatomical Scaffold and Bioreactor Chamber.

The grafts are designed based on the magnetic resonance or computer tomography images of the defect being repaired. The individual slices are converted into three-dimensional (3D) files using computer-aided software such as Mimics® Innovation Suite (Materialise, Belgium). After defining the exact anatomical fit for the graft being reconstructed, the 3D computer model of the graft is exported as a .STL file and used for the fabrication of the scaffold and the matching inner chamber of the bioreactor.

To fabricate the anatomical scaffold, the 3D model STL file is imported into the SolidWorks (Dassault Systemes SolidWorks, MA, USA) and a G-code for milling an anatomical scaffold from a block of material is generated using MasterCAM (CNC Software Inc., CT, USA) add-in in SolidWorks. The scaffold material used in the present study was the bovine trabecular bone harvested from calf knee after removing the muscles, patella, fibrous connective tissues, ligaments, and meniscus and leaving only the femur head exposed. Using a table-top band saw, articular cartilage and cortical bone were removed to isolate spongy trabecular bone. Using a lathe (LittleMachineShop, CA, USA), the bone was shaped into cylindrical blocks with a diameter just larger than the width of the 3D graft model and the length approximately 3 cm longer than the 3D model so that there is enough structure to hold the blocks during machining. We used a four-flute ¼" ball-end mill (McMaster-Carr, NJ, USA) to shape the anatomical bone scaffold from cylindrical bone block on the 4-axis CNC milling machine (LittleMachineShop, CA, USA). The anatomically shaped bone blocks were completely decellularized using hypotonic solution, detergent, multiple washes and DNAse/RNAse solution using a method we previously established.

Figure 27:
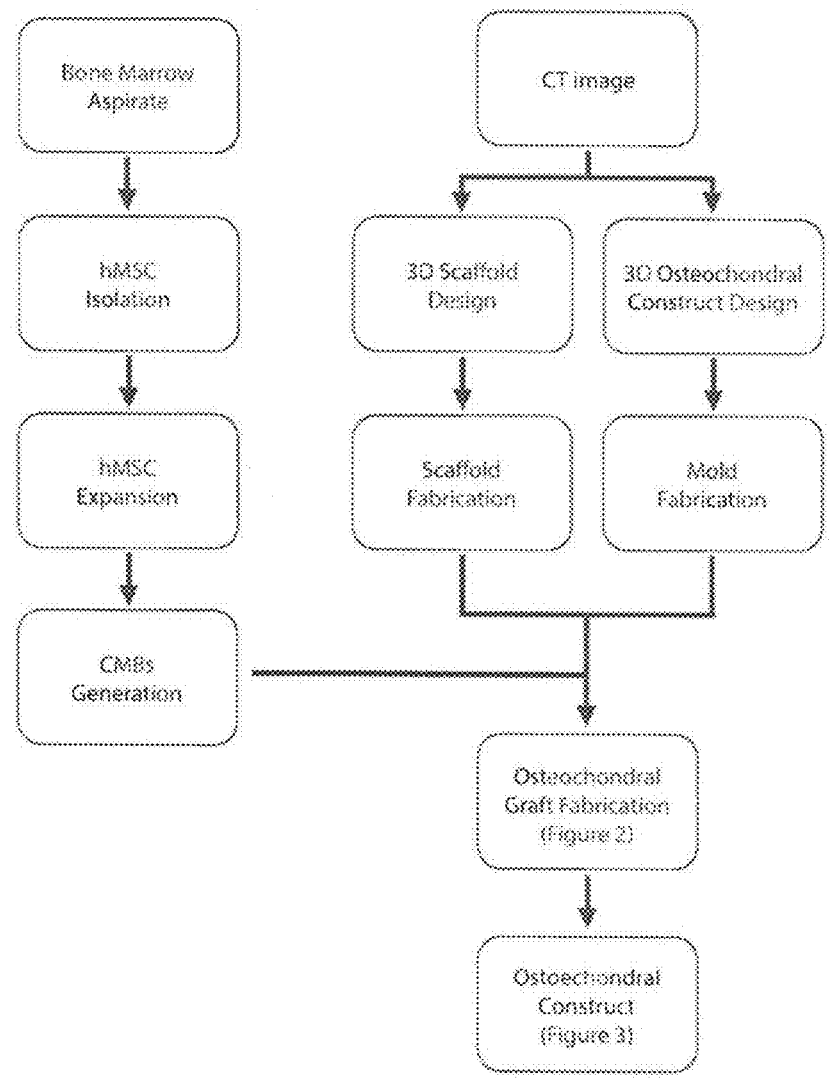
FIG. 27 is a flow chart with the steps of imaging-guided engineering of a human osteochondral constructs starting from condensing mesenchymal bodies (CMBs) that were derived from human mesenchymal stem cells, interfaced with an anatomically shaped scaffold and cultured in a matching bioreactor chamber.

The same 3D image of each anatomical graft was then used to design the mold for fabricating the inner bioreactor chamber for cultivating the osteochondral construct. The desired cartilage thickness was established over the articular surface by using the surface selection tool to set the shape of the articular surface in SolidWorks, and a desired thickness (in most cases 1 mm or more). The G-code was then created to mill a Teflon rod (McMaster-Carr, NJ, USA) to hold the construct. A negative mold was then made using the milled piece by pouring the SylGard® 184 Silicone Elastomer (Dow Corning, MI, USA) over the milled structure. Once cured, the silicone was cut into two pieces, one to hold the decellularized bone scaffold and the other to hold the condensed mesenchymal bodies (CMBs) that will be pressed inside the mold against the articulating surface. The two-piece mold was sterilized by autoclaving. The key steps of the process are schematically shown in FIG. 27.

Preparation of Bone-Marrow Derived Mesenchymal Stem Cells.

Fresh human bone marrow aspirates were obtained either from orthopaedic surgeries (through a non-human IRB for fully de-identified surgical materials) or from a commercial supplier such as Cambrex (NJ, USA). Mesenchymal stem cells (BMSCs) were isolated by attachment to the cell culture plastics, and expanded in DMEM supplemented with 10% FBS, 1% pen-strep, and 0.1 ng/mL basic fibroblast growth factor (bFGF). The cells were cultured up to the third passage and tested for the multi-lineage differentiation capability.

Generation of Condensed Mesenchymal Bodies.

After trypsinization, BMSCs were suspended in chondrogenic medium consisting of high-glucose DMEM supplemented with 100 nM dexamethasone, 50 µg/ml ascorbic acid-2-phosphate, 100 µg/ml sodium pyruvate, 40 µg/ml praline, a mix of 1% insulin, transferrin, and sodium selenite (ITS+), 1% penicillin/streptomycin, and 10 ng/ml Transforming Growth Factor-beta3 (TGF-133), at the concentration of $5 \times 10^5$ cells/ml. 1 ml cell suspension was added to the wells of a deep round-bottom 96-well plate (NUNC®, Sigma-Aldrich, MO.) and centrifuged at 25 g for 5 min. The cells were incubated overnight at 37° C. 15% CO2) to form spherical CMBs that were used to generate the cartilage layer of the osteochondral tissue construct.

Fabrication of the Tissue Constructs.

After 3 days of culture, the spherical CMBs grow to just above 1 mm in diameter. The number of CMBs used for each construct can be calculated from the volume of the cartilage layer that needs to be engineered, using Equation 1.

$$n = \frac{V_{cartilagte}}{\frac{4}{3}\pi (0.5)^2} \qquad \text{Equation 1}$$

Figure 28:
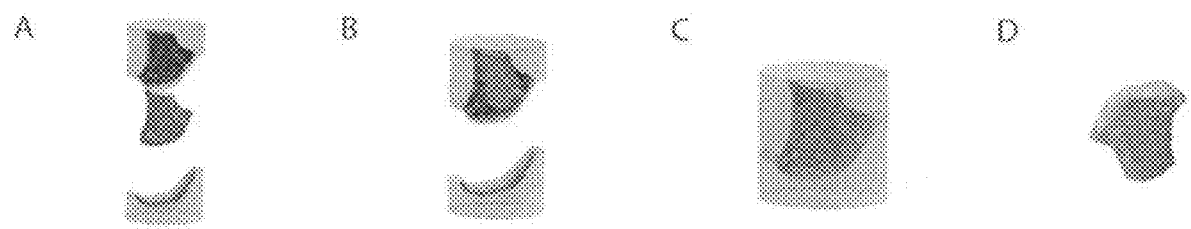
FIG. 28 depicts fabrication of osteochondral grafts according to embodiments of the present disclosure. A Silicone mold is made in two pieces, and the CMBs are placed at the articular side. B An anatomically shaped scaffold machined by image-guided processing of native bone matrix is then placed into the other side of the mold. C The two-piece mold is fused together, causing the mold to press the CMBs into a desired shape of an articular surface on the scaffold. D The two-Native-like histomorphology of human cartilage formed at the surface of bone. Phase osteochondral construct is then cultured in a matching, anatomically shaped bioreactor chamber.

For example, for a layer of articular cartilage that has a surface of 1 cm2 and 1 mm thick, on would need 190 CMBs that are transferred to the articular side of the mold. The anatomical scaffold is then inserted into the other side of the mold and slowly pressed onto the articular side (FIG. 28). By applying compressive force, the CMBs are made to fuse together and shaped at an even depth over the articular surface. It is important that a sufficient amount of the fused CMBs penetrates into the bone phase to drive the integration between the forming cartilage an bone. The osteochondral tissue construct was cultured for 5 weeks in chondrogenic media, using a medium volume of 100 µl per CMB, with a medium change twice a week.

After press molding, the fused CMBs formed a dense cellular layer on the surface of the bone substrate inside the mold. The initial construct consisted of two clearly distinguished layers: (i) a dense cellular layer that will form a cartilage surface following cultivation, and (ii) a bone substrate. The penetration of fused CMBs into the bone substrate created an interface that gradually interlocked the two layers by forming a stratified structure.

Figure 29:
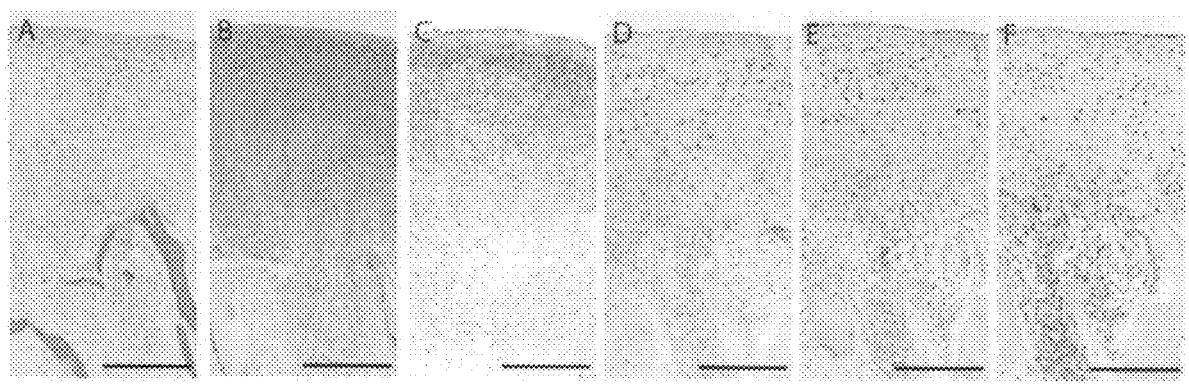
FIG. 29 shows native-like histomorphology of human cartilage formed from MSCs at the surface of the bone. After cultivation in chondrogenic medium for 5 weeks, the dense cellular layer developed into stratified cartilage. A H&E, B Alcian Blue, C Collagen type II, D Lubricin, E Collagen type I, and F Collage type X. [Bar: 500 μm].

Following the 5 weeks of cultivation in chondrogenic medium, an osteochondral tissue construct formed, with a dense layer of cartilaginous tissue, a bone tissue underneath and an interface in between (FIG. 29). These constructs exhibited a very well developed stratified structure with a native-like gradient of structural and compositional properties from the cartilage to the bone region. The cartilage region was rich in glycosaminoglycans and collagen type II, the main components of native articular cartilage, while collagen type I was mostly present in the bone region (FIG. 29). Notably, lubricin, a protein essential for lubrication of the articulating cartilage surfaces, was present at the superficial surface of the cartilage layer.

The interface consisted of cells residing in the scaffold pores that deposited only minimal amount of glycosaminoglycan and collagen type II, and instead were surrounded collagen type I and collagen type X, indicating the formation of calcified cartilage.

This method resulted, for the first time, in cartilage engineered from human MSCs that achieved mechanical properties in physiological range. Both the Young modulus measured in compression and the friction coefficients measured in tribological studies of the tissue engineered cartilage were comparable to those measured in young native cartilage (Table 3).

TABLE 3

Mechanical properties of tissue engineered cartilage (16) and native cartilage

| | Engineered cartilage | Native cartilage |
|---|---|---|
| Young modulus (kPa) | ~800-850 | 949 |
| Minimum friction coefficient | ~0.046-0.049 | 0.0156 |
| Equilibrium friction coefficient | ~0.276-0.283 | 0.3 |

The methods described herein utilize the mechanism of self-assembly of BMSCs with special regard to the mechanisms underlying the native process of mesenchymal condensation that precedes cartilage formation during limb development. This technique requires understanding of the setting of the outer boundary by the condensing BMSCs. After forming a spherical cell body, the BMSCs begin to differentiate and deposit the extracellular matrix. One of key components of this matrix is tenascin, the boundary setting protein deposited during the mesenchymal condensation that sets the tissue boundaries.

During BMSCs condensation in vitro, tenascin starts to accumulate at outer surfaces of the spheroids the periphery by day 5 post condensation, which was an indication for the setting of boundary. The setting of these outer boundaries on mesenchymal bodies prevented their fusion even when they were pressed against each other. This in turn suggests that larger volumes of cartilage, alone or within osteochondral constructs, could only be produced if fusion is induced within 5 days of spheroid formation.

Indeed, the press-molding of the mesenchymal bodies formed by the condensation of BMSCs (FIG. 28) results in dense and spatially uniform layer of cells. This dense cellular layer resembles the layers that form in vivo during native mesenchymal condensation, and that serve as a platform for cartilage formation. In vitro, these compact layers with very high cell density induce rapid deposition of extracellular matrix. As a result, the engineered tissue became mechanically strong, and both the Young's modulus and the friction coefficient reached physiological levels (Table 3). At the same time, the compacted cell layer developed into physiologically stratified cartilage containing lubricin at the surface, proteoglycans and type II collagen in the bulk phase, collagen type X at the interface with the bone substrate, and collagen type I within the bone phase (FIG. 29).

Thus, the fusion of mesenchymal bodies formed from BMSCs at the interface with a bone substrate can be an effective method for generating human osteochondral tissue constructs with physiological compositions, histomorphologies and mechanical properties. This approach enables, the human cartilage grown from BMSCs to reach physiological stiffness and friction coefficient. Also, the methods allows engineering of anatomically-shaped osteochondral constructs generated using scaffolds made by imaging-guided fabrication.

The reconstruction of 1 cm$^2$ of the cartilage surface, with the thickness of cartilage layer of 2 mm, requires almost 100 million BMSCs. To reconstructs a whole condyle, one would need hundreds of millions of cells. To reduce this number, mesenchymal condensation may be combined with the use of scaffolds, and the utilization of easily accessible and abundant sources of mesenchymal cells, such as the adipose tissue.

While the disclosed subject matter is described herein in terms of certain exemplary embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A medical device comprising,
   engineered human cartilage, wherein the engineered human cartilage has a Young's modulus greater than about 400 kPa and an equilibrium friction coefficient less than about 0.4, and wherein the engineered cartilage consists essentially of: condensed mesenchymal bodies; cartilage extracellular matrix; cartilage; and a scaffold consisting of decellularized bone matrix.

2. The medical device of claim 1, wherein the engineered human cartilage is attached to a bone substrate.

3. The medical device of claim 1, wherein the engineered human cartilage is anatomically shaped.

4. The medical device of claim 1, wherein the engineered human cartilage is centimeter sized.

5. The medical device of claim 1, wherein the engineered human cartilage includes physiological stratification properties.

6. The medical device of claim 1, wherein the engineered human cartilage has stiffness and tribological properties.

7. The medical device of claim 1, wherein the engineered human cartilage is disposed in a delivery device.

8. The medical device of claim 7, wherein the delivery device is an injector pen.

9. The medical device of claim 2, wherein the bone substrate is an articular surface of a condyle.

10. The medical device of claim 9, wherein the condyle corresponds to an anatomical human condyle of a patient, and the medical device is a personalized osteochondral tissue construct for the patient.

11. The medical device of claim 2, wherein the bone substrate has the contour of a condyle.

12. The medical device of claim 1, wherein the engineered human cartilage has a Young's modulus greater than about 600 kPa and an equilibrium friction coefficient less than about 0.3.

* * * * *